United States Patent [19]
Hoefer

[11] 4,048,049
[45] Sept. 13, 1977

[54] TUBE GEL ELECTROPHORESIS DEVICE

[75] Inventor: Stanton A. Hoefer, San Francisco, Calif.

[73] Assignee: Hoefer Scientific Instruments, San Francisco, Calif.

[21] Appl. No.: 743,483

[22] Filed: Nov. 19, 1976

[51] Int. Cl.² .......................................... G01N 27/26
[52] U.S. Cl. ............................ 204/299 R; 204/180 G
[58] Field of Search ............... 204/180 G, 180 R, 299; 23/230 B

[56] References Cited

U.S. PATENT DOCUMENTS

| | | | |
|---|---|---|---|
| 3,699,033 | 10/1972 | Zeineh | 204/299 X |
| 3,773,648 | 11/1973 | Welzen et al. | 204/299 |
| 3,867,271 | 2/1975 | Hoefer | 204/180 G |
| 3,950,546 | 9/1976 | Caccavo | 204/299 |
| 3,956,099 | 5/1976 | Israel et al. | 204/299 |

Primary Examiner—Arthur C. Prescott
Attorney, Agent, or Firm—Flehr, Hohbach, Test, Albritton & Herbert

[57] ABSTRACT

A device for performing electrophoretic separation of samples in a tube shaped gel. An outer container has an open upper end and side walls joined by a bottom closure. An upper buffer chamber assembly is received in and supported by the open upper end of the outer container. The upper buffer assembly defines an upper buffer chamber therein having a bottom wall spaced from the bottom closure of the outer container and thereby together with the outer container sidewalls forming a lower buffer chamber. A removable cooling core is disposed in the lower buffer chamber and has a cooling passage therethrough having open ends in communication with the lower buffer chamber. A plurality of tubes for holding electrophoresis separation gels are provided which extend through the bottom wall of the upper buffer chamber, thereby having one end in communication with each of the upper and lower buffer chambers. An electrode is provided in each of the buffer chambers so that when buffer solution is contained in each buffer chamber and voltage is impressed across the electrodes, the sample is electrophoretically separated in the separation gel in the tubes and heat energy generated within the separation gels is passed to the buffer solution in the lower buffer chamber. Circulation of the buffer solution through the cooling passages in the cooling core in turn transfers the heat energy to a coolant passing therethrough.

14 Claims, 8 Drawing Figures

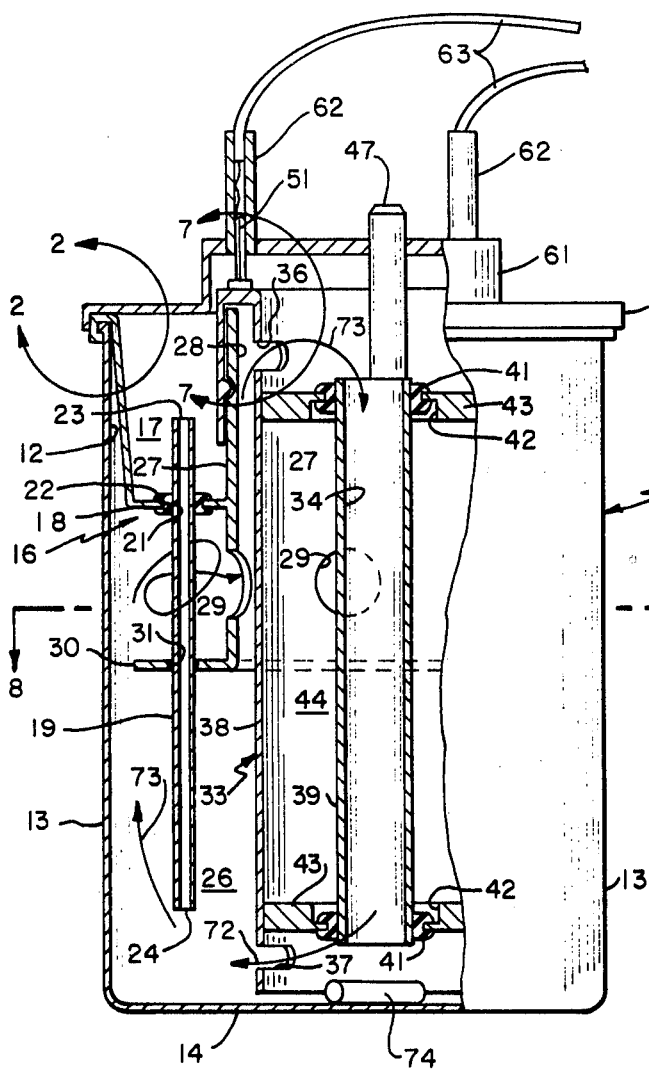
FIG.—1
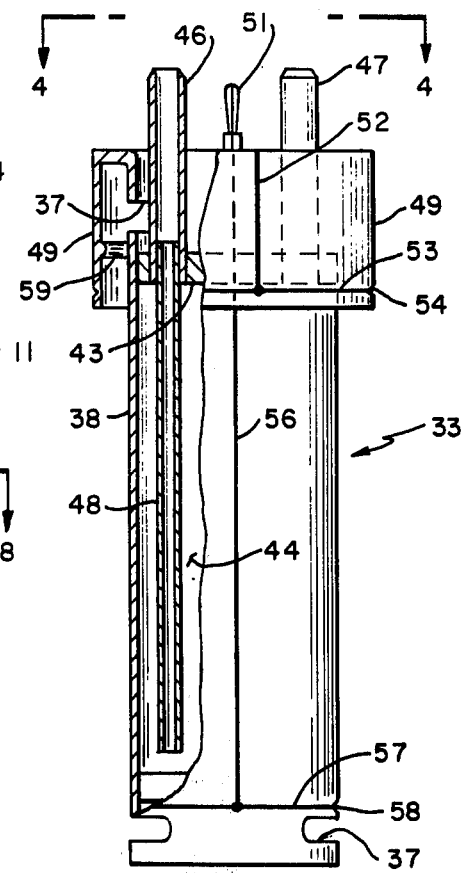
FIG.—3
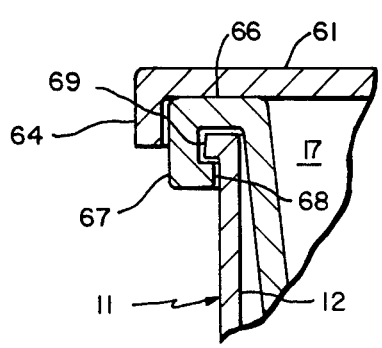
FIG.—2
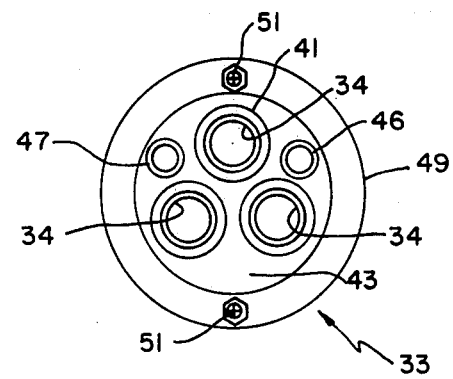
FIG.—4

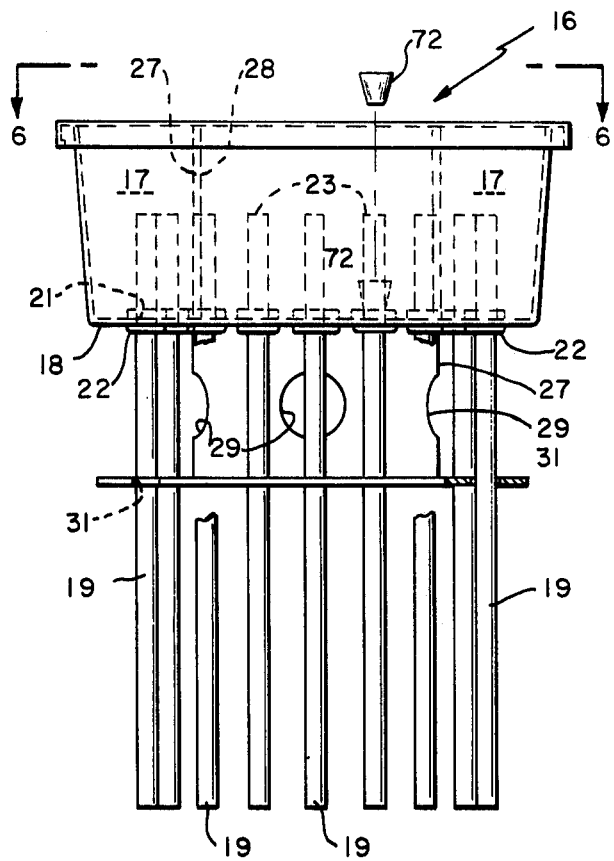
FIG.—5
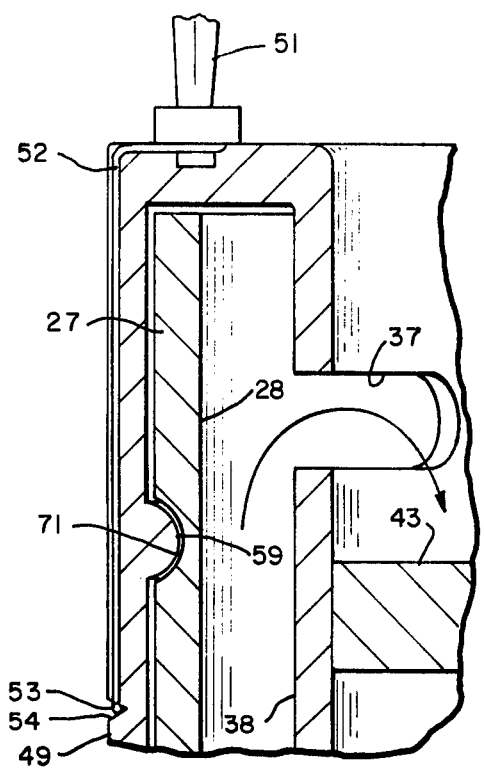
FIG.—7
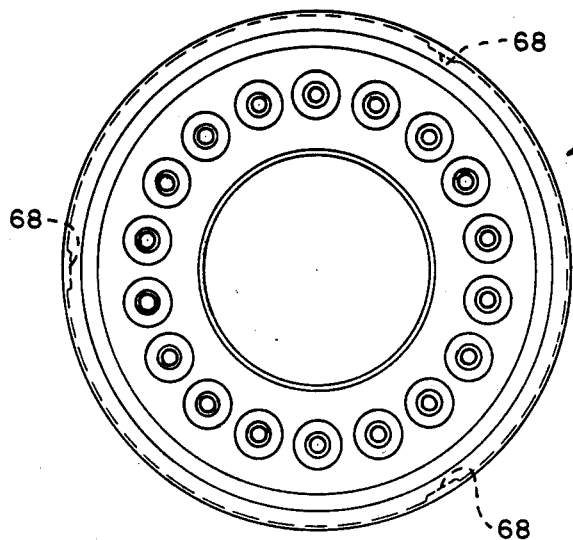
FIG.—6
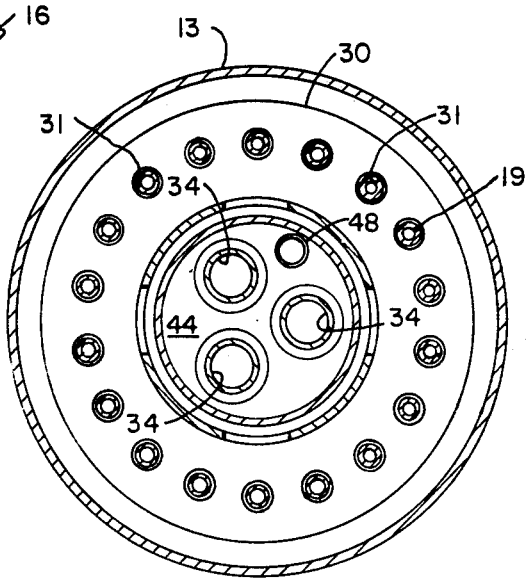
FIG.—8

TUBE GEL ELECTROPHORESIS DEVICE

BACKGROUND OF THE INVENTION

This invention relates to improved apparatus for tube gel electrophoresis for use in biochemical research and analysis.

Generally, devices for processing samples electrophoretically in separation gels are capable of processing one or more samples simultaneously, and usually include provision for maintaining a relatively constant temperature in the gel during the separation process. One such apparatus is disclosed in the present inventor's U.S. Pat. No. 3,867,271. Such a device must be completely assembled to define upper and lower buffer chambers and cooling chambers for controlling the temperature of the tube gels during electrophoresis. Consequently, the entire apparatus must be drained and disassembled to remove a single one of the tubes if it is desirable to terminate the separation process in any one of the gels contained therein. The disassembly is time consuming and untidy. Great convenience would be provided if an apparatus was available having separate unitary upper and lower buffer chambers and a cooling chamber so that assembly and disassembly of the apparatus could be undertaken with the chambers filled with buffer and cooling solutions respectively.

SUMMARY AND OBJECTS OF THE INVENTION

In general the disclosed improved tube gel electrophoresis apparatus has an outside container with an upper opening and a closed lower end with sidewalls which at the closed lower end define a lower buffer chamber. An upper buffer chamber assembly contains an upper buffer chamber which has a bottom wall which is common with the lower buffer chamber when the upper buffer chamber assembly is received and supported in the upper opening of the outer container. A cooling core is located within the outer container and extends into the lower buffer chamber. A heat transfer passage is formed through the cooling core. The passage has opposing ends which are each in communication with the lower buffer chamber. A number of gel tubes extend through in sealed relation with the bottom wall of the upper buffer chamber, thereby exposing one end of each tube to the upper buffer chamber and the opposite end of each tube to the lower buffer chamber. An electrode is disposed in each of said lower and upper buffer chambers and an inlet and outlet are provided for cooling to the cooling core. Consequently, when buffer solutions are placed in each of the buffer chambers and the solution in the lower buffer chamber is circulated past the gel tubes extended therein, the heat generated within the gel during electrophoresis is removed by the circulating buffer solution and transferred in the passage through the cooling core to a coolant circulated therethrough.

It is an object of the present invention to provide an improved tube gel electrophoresis apparatus which may be assembled and disassembled without draining buffer and coolant solutions therefrom.

It is another object of the present invention to provide an improved tube gel electrophoresis unit in which individual tubes may be removed from the assembly without draining any of the buffer or the coolant solutions.

It is another object of the present invention to provide an improved tube gel electrophoresis unit having interchangeable upper buffer chamber assemblies carrying different sizes of gel tubes therein.

Additional objects and features of the invention will appear from the following description in which the preferred embodiment has been set forth in detail in conjunction with the accompanying drawings.

BRIEF DESCRIPTION OF THE DRAWINGS

FIG. 1 is a side elevational view partially sectioned of the improved tube gel electrophoresis apparatus.

FIG. 2 is an enlarged sectional detail view along the arc 2—2 of FIG. 1.

FIG. 3 is a side elevational view partially sectioned of a disclosed cooling core.

FIG. 4 is a plan view along the line 4—4 of FIG. 3.

FIG. 5 is a side elevational view of a disclosed upper buffer chamber assembly.

FIG. 6 is a plan view along the line 6—6 of FIG. 5.

FIG. 7 is an enlarged sectional detail view along the arc 7—7 of FIG. 1.

FIG. 8 is a sectional view along the line 8—8 of FIG. 1.

DESCRIPTION OF THE PREFERRED EMBODIMENT

The device for performing electrophoretic separation of a sample in a tube gel is shown in FIG. 1 as having an outer container 11 with an upper open end 12 and sidewalls 13 having a bottom 14 extending therebetween to form a lower closed end. Shown supported in upper open end 12 is an upper buffer chamber assembly 16. Upper buffer assembly 16 has an upper buffer chamber 17 therein which receives and retains a buffer solution. Upper buffer chamber 17 has a bottom wall 18 having a plurality of gel tubes 19, one of which is shown in FIG. 1, extending therethrough. A plurality of apertures 21 are formed in bottom wall 18 for allowing passage of gel tubes 19. A plurality of resilient seals 22 disposed one each in each aperture 21. The resilient seals 22 bar passage of fluid across bottom wall 18. Gel tubes 19 have an upper open end 23 exposed to upper buffer chamber 17 and a lower open end 24 exposed to a lower buffer chamber 26 defined by sidewalls 13 and bottom 14 of outer container 11.

Upper buffer chamber assembly 16 has an inner cylindrical wall 27 which defines one limit of upper buffer chamber 17. Upper buffer chamber 17 is therefore annular in shape opening upwardly as shown and having a central opening 28 therethrough. Inner cylindrical wall 27 extends below bottom wall 18 having openings 29 therethrough. A lower disc-like platform 30 is attached to the bottom end of inner cylindrical wall 27 having holes 31 therein individually aligned with apertures 21 in bottom wall 18. Holes 31 serve to support the lower end of gel tubes 19 and to prevent lateral movement thereof, since the major portion of the length of tubes 19 extends below bottom wall 18.

A cooling core 33 is disposed in lower buffer chamber 26 extending through central opening 28 in upper buffer chamber assembly 16 and being supported by contact with the upper edge of inner cylindrical wall 27. Cooling core 33 has a passage 34 extending therethrough which is in communication with lower buffer chamber 27 at the upper and lower end thereof through openings 36 and 37 respectively in a sidewall 38 in cooling core 33. Passage 34 is formed by the wall of a tube 39 which is supported by a resilient sealing grommet 41 in an opening 42 through upper and lower cooling core walls 43. A coolant reservoir 44 is defined by cooling core sidewall 38 between upper and lower cooling core walls 43. More than one passage 34 may be formed through coolant reservoir 44 to improve the rate of heat transfer between a medium passing through coolant passages 34 and a medium circulated through coolant reservoir 44.

FIG. 3 shows unitary cooling core 33 having an inlet fitting 46 and an outlet fitting 47 extending through upper cooling core wall 43 into coolant reservoir 44. Inlet fitting 46 has coupled thereto a depending pipe 48 which deposits incoming coolant near the bottom of coolant reservoir 44 to improve circulation thereof. Outlet fitting 47 removes coolant from coolant reservoir 44 near the top thereof to thereby carry away heat transferred to the coolant through the walls of cooling passage 34 formed by tube 39. Cooling core 33 also has a depending upper skirt 49 spaced from the outer surface of sidewall 38 and extending around the periphery of the upper end thereof. A pair of male electrical terminals 51 are shown mounted at the junction between wall 38 and the depending upper skirt 49 on cooling core 33. One of the male terminals 51 is shown connected by a conductor 52 to an upper electrode 53 disposed in a notch 54 extending around the outer periphery of depending upper skirt 49. Another conductor 56 is shown extending down the outer surface of wall 38 being connected to a lower electrode 57 disposed in a notch 58 extending around the outer periphery of the lower end of wall 38. A bead 59 is shown formed on the inner periphery of depending upper skirt 49 for a purpose to be hereinafter disclosed.

FIG. 1 shows a cover 61 having two female electrical connectors 62 mounted therein and aligned one each with each of the male terminals 51 which extend upwardly from the upper edge of cooling core 33 as described above. A conductor 63 leads from each of the female electrical terminals 62, so that a voltage may be impressed between upper and lower electrodes 53 and 57 respectively. Cover 61 has a depending peripheral lip 64.

FIG. 2 shows the manner in which upper buffer chamber assembly 16 is supported in the upper open end 12 of outer container 11. Cover 61 and depending peripheral lip 64 are shown overlying an outer peripheral edge 66 on upper buffer chamber assembly 16. Depending from outer peripheral edge 66 is a peripheral lip 67 which has several inwardly projecting teeth 68 formed thereon. Upper open end 12 has an outwardly projecting bead 69 therearound with spaces (not shown) therein which allow inwardly projecting teeth 68 to pass therethrough. It may be seen that once inwardly projecting teeth 68 through the spaces in outwardly projecting beads 69, and depending peripheral lip 67 is rotated on upper open end 12, upper buffer chamber 16 is secured in place within upper open end 12.

Once upper buffer chamber assembly 16 is positioned in upper open end 12 of outer container 11, cooling core 33 is dropped through central opening 28 so that upper depending skirt 49 extends downwardly adjacent to the outer surface of inner cylindrical wall 27 as best shown in FIG. 7 of the drawings. A groove 71 is formed about the outer periphery of inner cylindrical wall 27 in a position such that bead 59 mates therewith when cooling core 33 is inserted through central opening 28 to extend into lower buffer chamber 26. It may be seen that cooling core 33 is held in place within central opening 28 when bead 59 is in groove 71. Cooling core 33 may be removed from central opening 28 by forceably pulling cooling core 33 in an axial direction until bead 59 snaps out of groove 71. It should also be noted that wall 38 on cooling core 33 is spaced from the surface of central opening 28 through upper buffer chamber assembly 16.

A number of passages 34 may be formed through coolant reservoir 44 as mentioned above. FIG. 4 shows three such passages 34 passing through resilient sealing grommets 41. The multiple cooling passages 34 provide for a greater rate of heat exchange between a fluid passing therethrough and a coolant circulated through coolant reservoir 44.

FIG. 5 shows the plurality of gel tubes 19 situated in upper buffer chamber assembly 16 having their upper open ends 23 exposed to upper buffer chamber 17. Upper buffer chamber assembly 16 is designed so that various assemblies may carry different sizes of gel tubes 19 so that different assemblies 16 may be inserted at different times within outer container 11 and supported at the upper open end 12 thereof. Also, as shown in FIG. 5, a plug 72 is provided which may be brought to bear against the upper open end 23 of one of the gel tubes 19 while an upper buffer solution is present in upper buffer chamber 17. With upper buffer chamber assembly 16 withdrawn from outer container 11 plug 72 may be brought to bear against upper end 23 of gel tube 19 pushing it downwardly through resilient seal 22 until it is released therefrom and resilient seal 22 simultaneously engages the periphery of plug 72. In this fashion upper buffer solution is prevented from escaping from upper buffer chamber 17 through seals 22 during and after removal of a gel tube 19.

FIG. 6 shows the inwardly projecting teeth 68 on the depending peripheral lip 67 of upper buffer chamber assembly 16. Teeth 68 may be situated at some convenient arc separation about the periphery of lip 67 in position to match openings in outwardly projecting bead 69 at upper open end 12 on outer container 11. As described above it may be seen that after teeth 68 have passed through the openings in bead 69 and upper buffer chamber assembly 16 is rotated through some arc, upper buffer chamber assembly 16 is locked within upper open end 12 and will not be released until teeth 68 are once again aligned with the openings through beads 69, and upper buffer chamber assembly 16 withdrawn axially therefrom.

FIG. 8 shows the lower disc-like platform 30 on upper buffer chamber assembly 16 having apertures 31 therethrough for retaining gel tubes 19 laterally. Moreover, FIG. 8 also shows depending pipe 48 in coolant reservoir 44 and multiple cooling passages 34 therethrough. Note that a space exists between side walls 13 of outer container 11 and the edge of lower disc-like platform 30.

With the foregoing description in mind it may be seen that three unitary sections are provided in the device disclosed herein for performing electrophoretic separation in tube gels. Outer container 11 forms a lower buffer chamber 26 in the lower end thereof into which lower buffer solution may be poured whether upper buffer chamber assembly 16 is in place or not. Upper buffer chamber assembly 16 is also a unitary assembly containing upper buffer chamber 17 in which upper buffer solution may be placed after tubes 19 or plugs 72 occupy each of the openings through resilient seals 22. Cooling core 33 is also a unitary assembly and may be secured to upper buffer chamber assembly 16 as hereinbefore described without regard to the presence of coolant within coolant reservoir 44 contained therein.

Operation of the disclosed device proceeds as follows. Outer container 11 is filled with an amount of lower buffer solution and upper buffer chambers assembly 16 containing gel tubes with separation gels and samples therein is inserted into upper open end 12 and locked in place. Cooling core 33 is thereafter inserted through central opening 28 and secured in place in upper buffer chamber assembly 16 as described above. Upper buffer chamber 17 is filled with a buffer solution to a predetermined level. Lower buffer chamber 26 is "topped off" by pouring lower buffer solution through passages 34 until lower buffer solution level rises on side-wall 38 to at least upper opening 36 and preferably to a level in central opening 28 which coincides with the predetermined level of buffer solution in upper buffer chamber 17. Cover 61 is placed over the entire assembly assuring contact between male connectors 51 and female connectors 62. Inlet and outlet fittings 46 and 47 respectively extend through cover 61 and a coolant source is connected thereto. Coolant flow is begun and power is applied through conductor 63 to impress a voltage between the upper and lower buffer solutions in upper and lower buffer chambers 17 and 26 respectively. Electrophoretic separation of the samples takes place within the separation gels in tubes 19, and lower buffer solution surrounds the major portion of gel tubes 19. Consequently, the heat of electrophoresis is transferred to the lower buffer solution which thermally circulates as indicated by arrows 73. Alternatively, lower buffer solution is circulated by agitation such as is provided by a magnetically operated stirring bar 74 which urges solution through lower opening 37. Arrows 73 are shown passing from lower buffer chamber 26 around the body of gel tube 19 to the space between central opening 28 and cooling core wall 38. Thereafter lower buffer chamber solution passes through upper opening 36, through cooling passage 34, descending to exit through lower opening 37 into lower buffer chamber 26 once again. Heat removed from the gels being processed in tubes 19 is carried by lower buffer solution through passage 34 where it is transferred through the wall of tube 39 to coolant being circulated through coolant reservoir 44. In this fashion the temperature of the gels in gel tube 19 is maintained at a relatively stable level through the electrophoresis process.

A tube gel electrophoresis device has been disclosed for use in biochemical research and analysis which has interchangeable upper buffer chambers to accommodate a variety of gel tube sizes. The apparatus also discloses structure providing highly effective controlled cooling during the electrophoresis process and provides for selective removal of gel tubes while the electrophoresis run is in progress.

What is claimed is:

1. Tube gel electrophoresis apparatus, comprising:
   an outer container having an upper open end and a lower closed end,
   an annular inner container having an upper open end and lower closed end,
   said annular inner container forming an upper buffer chamber therewithin and being supported at the upper open end of said outer container forming a lower buffer chamber therebetween,
   a plurality of gel holding tubes sealably passing between and having opposed open ends exposed one each to said upper and lower buffer chambers said gel holding tubes having most of their length disposed in said lower buffer chamber,
   a cooling core extending through said annular inner container into said lower buffer chamber, said cooling core having a cooling passage therethrough communicating with said lower buffer chamber and further having a contained coolant chamber therein,
   an upper and lower buffer chamber electrode in each of said upper and lower buffer chambers respectively,
   means for conducting a coolant to and from said contained coolant chamber
   said lower buffer chamber and cooling core providing a path for circulating a buffer solution in said lower buffer chamber through said cooling passage, whereby heat generated in gels in said gel tubes during electrophoresis is conducted away by the circulating lower buffer solution and transferred in said cooling passage to the coolant.

2. Tube gel electrophoresis apparatus as in claim 1 together with means for locking said annular inner container in position at the upper open end of said outer container.

3. Tube gel electrophoresis apparatus as in claim 1 together with means for retaining said cooling core in position relative to said annular inner container.

4. Tube gel electrophoresis apparatus as in claim 1 together with additional cooling passages through said cooling core communicating with said lower buffer chamber, whereby heat transfer between the circulating lower buffer solution and the coolant is further facilitated.

5. Apparatus for electrophoretic separation of samples in tube gels comprising,
   an outer container having an upper opening therein with a closed lower end and side walls defining a lower buffer chamber,
   an upper buffer chamber assembly defining an upper buffer chamber having a bottom wall common with said lower buffer chamber, said upper buffer chamber assembly being received and supported in said upper opening,
   a cooling core disposed within said outer container extending into said lower buffer chamber,
   a heat transfer passage through said cooling core having opposing ends in communication with said lower buffer chambers,
   a plurality of gel tubes sealably extending through said bottom wall, thereby having opposite ends exposed to said upper and lower buffer chambers respectively, said gel tubes being adapted to receive gels and samples for electrophoresis,
   a lower electrode in said lower buffer chamber, an upper electrode in said upper buffer chamber,
   and an inlet and outlet for a coolant in said cooling core,
   whereby when a buffer solution is circulated in said lower buffer chamber during electrophoresis it contacts said gel tubes removing heat therefrom and passes through said heat transfer passage to transfer the heat to the coolant.

6. Apparatus as in claim 5 together with a plurality of resident seals in said bottom wall surrounding one each of said plurality of gel tubes, whereby ones of said gel tubes are removable therefrom.

7. Apparatus as in claim 5 together with means for locking said upper buffer chamber assembly in said upper opening, so that said upper buffer chamber assembly is removable from said outer container when said means for locking is released.

8. Apparatus as in claim 5 together with means for releasably securing said cooling core to said upper buffer chamber assembly, whereby said cooling core is removable when said means for securing is released.

9. Apparatus as in claim 8 wherein said upper buffer chamber is an annular and said cooling core extends through the center of said annular having contacting surfaces therebetween, said means for releasably securing comprising a matching peripheral ridge and groove on said contacting surfaces.

10. Apparatus as in claim 5 wherein the levels of buffer solutions in said upper and lower buffer chambers are the same, thereby providing substantially zero pressure differential across a gel having density similar to the density of the buffer solutions.

11. Apparatus for performing electrophoresis in tube gels, comprising
an upper buffer chamber assembly defining an upper buffer chamber therein,
an outer container having a closed lower end, side walls and an upper opening, said upper opening being formed to receive and support said upper buffer chamber assembly therein,
a removable cooling core disposed within said outer container having an inlet and an outlet for coolant,
means cooperating between said upper buffer chamber assembly and said cooling core for securing one to the other,
said upper buffer chamber assembly including a bottom wall forming a lower chamber between said side walls and closed lower and of said outer container, a plurality of open ended gel tubes extending through said bottom wall so that a major portion of the length of said gel tubes lies within said lower buffer chamber, a plurality of seals disposed one each between each of said plurality of gel tubes and said bottom wall, said removable cooling core having a cooling passage therethrough in communication with said lower buffer chamber at opposite ends, and an electrode in each of said upper and lower buffer chambers, so that when gels and samples are contained in said plurality of gel tubes and a voltage is applied between said electrodes while buffer solutions are contained in said upper and lower buffer chambers, lower buffer solution circulating by said gel tubes removes heat energy from said gels and transfers it to coolant in said removable cooling core as it passes through said cooling passage.

12. Apparatus as in claim 11 together with releasable means for holding said upper buffer chamber assembly in said upper opening so that said upper buffer chamber assembly is removable when said means for holding is released without draining said upper and lower buffer chambers.

13. Apparatus as in claim 11 together with means for circulating the buffer solution is said lower buffer chamber whereby rate of heat energy transfer from the gels to the coolant is increased.

14. Apparatus as in claim 11 wherein said removable cooling core has additional cooling passages therein, whereby rate of heat energy transfer from the gels to the coolant is increased.

* * * * *